United States Patent [19]

Trabucco et al.

[11] Patent Number: 5,243,977
[45] Date of Patent: Sep. 14, 1993

[54] PACEMAKER

[76] Inventors: Héctor O. Trabucco, 2926 Sante Fe Avenue, 6th Fl. "B", 1425 Buenos Aires, Argentina; Jordán Gavrielides, 4029 Rocamora St., 1184 Buenos Aires, Argentina

[21] Appl. No.: 721,284

[22] Filed: Jun. 26, 1991

[51] Int. Cl.$^5$ ............................................. A61N 1/362
[52] U.S. Cl. ...................................... 607/10; 607/120; 607/129
[58] Field of Search ...................... 128/419 P

[56] References Cited

U.S. PATENT DOCUMENTS

| | | | |
|---|---|---|---|
| 4,157,720 | 6/1979 | Greatbatch | 128/419 P |
| 4,256,115 | 3/1987 | Bilitch | 128/419 P |

FOREIGN PATENT DOCUMENTS

| | | | |
|---|---|---|---|
| 507325 | 4/1976 | U.S.S.R. | 128/419 P |
| 1161579 | 8/1969 | United Kingdom | 128/419 P |

OTHER PUBLICATIONS

Loh, Ih Houng, Sc. D. "Conducting-polymer Bioelectrode", Medical Electronics, Feb. 1991.

Primary Examiner—William E. Kamm
Assistant Examiner—Scott M. Getzow
Attorney, Agent, or Firm—Helfgott & Karas

[57] ABSTRACT

The pacemaker includes a casing housing a pulse generator having at least one electrode tip preferably projecting out of said casing and being insulated therefrom, whereby no plug-receptacle nor electrode catheter is required. The pacemaker is to be surgically located below the heart in the virtual cavity formed between the epicardium and the pericardium with its electrode tip in close contact with the epicardium of the heart.

14 Claims, 3 Drawing Sheets

PACEMAKER

FIELD OF THE INVENTION

The present invention relates to a pacemaker to be used for stimulating, by direct contact, the epicardium and eventually the myocardium of the heart, as well as it refers also to a method of direct contact implanting said pacemaker in an optimum position onto the epicardium of the heart.

More particularly, the pacemaker of the present invention has one or several stimulating electrode tips incorporated into the pacemaker's casing, said electrode tip(s) being accessible from outside.

The terminology used in this particular art is not uniform throughout the world; in order to avoid any misunderstanding in connection with this specification and its appendant claims, the following terminology will be used:

The heart is a muscle consisting of three layers, an outer layer called "epicardium", an intermediate layer called "myocardium" and an inner layer called "endocardium", which actually circumscribes the ventricular and auricular chambers of the heart.

The expression "electrode tip" is generally used in this art, as refering to the free end of an insulated wire called "electrode" or "catheter", which in the known pacemaker is connected by its opposite or connecting end to the pacemaker's terminal or connector, housed in a plug-receptacle forming part of the pacemaker's casing and being accessible from outside—see U.S. Pat. Nos. 4,848,346 (K. F. Crawford) and 4,818,173 (T. D. Daglow). The electrode tip is destined to be connected to the heart either to its outside layer or epicardium or through a pervenous implantation to the endocardium. In short, the electrode tip is the tip through which electric current is supplied to stimulate the heart muscle by the pertinent source and electric circuit housed in the pacemaker's housing.

BACKGROUND OF THE INVENTION

According to the information available to us, since 1958, the year corresponding to the first permanent implantation of a pacemaker (see: Historical aspects of the cardiac pacing in "Cardiac Pacing", Escher, D. second edition—page 631—Ed. Samet-El-Sherif, Grune and Stratton, N.Y., 1980, U.S.A.), and up to now, all pacemaker implantations require an electrode or catheter to stimulate the heart. Said electrode may be monopolar or bipolar, as is well known by those skilled in the art.

Such electrode or catheter, upon being monopolar, consists of a helical and very resilient "electric wire", one of the ends of which, namely the one opposite to the aforementioned tip, is to be connected to said plug-receptacle, while the aforementioned tip is to be connected to the heart muscle itself. In these known electrodes, the electric wire is housed in an electrically insulating sheath, with the exception of the aforementioned connecting end and tip.

According to statistics, nowadays the stimulation failures range between 0.5 and 9% produced by the pacemaker's circuitry. On the other hand, failures originated by the electrode itself are much higher, since they range between 2 and 18% (see "Marcapasos Cardíacos'"—Cardiac Pacemakers—Trabucco, H. O. and adts. Ed. "El Ateneo"—page 146, 1989, Buenos Aires, Argentina).

It may be added, that the length of such an electrode ranges usually between 30 and 70 cm. The failures in those known electrodes or catheters are usually due to:

a) Failures in relationship to the fixation of the connecting end of the electrode in the plug-receptacle of the pacemaker's housing.

b) Failures, due to breaking, wearing, tearing or ageing of the insulating sheath, bearing in mind that the electrode is subject to mechanical and chemical stresses.

c) Failures, due to breaking of the electrode.

d) Failures, due to electrode tip dislocations from the selected implantation, which often generates cardiac arrest or potentially dangerous cardiac arrythmias.

e) Failures, due to perforating the heart muscle during implantation or during the immediate follow-up.

f) Failures, due to increase of the electric resistance or high threshold in the interface electrode tip/heart muscle developing an "exit block", which high threshold can be reduced using the FIG. 4 embodiment of the present invention, as will be later explained.

All these failures or complications lead to an irregular functioning of the stimulating system, which can be temporary or even permanent. In both cases it threatens the patient's life. Since the proposed pacemaker does not require a catheter, failures a) to e) become non-existant.

SUMMARY OF THE INVENTION

Bearing in mind all the above described drawbacks, extensive investigations and tests have been carried out, in order to develope a stimulating system not requiring a catheter or electrode, but merely an electrode tip.

Thus the pacemaker itself may be reduced in size, since it does not require a plug-receptacle housing to fix the electrode, which as already stated, is disposed of.

Accordingly, a pacemaker has been conceived, which may be used for direct heart stimulation, comprising a casing housing a pulse generator which is connected to at least one electrode tip forming part of the outside surface of the casing of the pacemaker and being electrically insulated therefrom, said electrode tip being capable of directly entering in pulse transmitting contact with the epicardium of the heart.

The electrode tip or the insulating portion surrounding part of said tip, may be provided with means, to house biomedical interesting materials, such as hormones which by means of a remote control may be released at will, in order to supply medication to the heart, if required.

Controlled relase drug delivery devices have already been proposed for other purposes and it has been shown that they do not have any adverse effects (see: Ih Houng Loh, Sc.D. "Conducting-polymer bioelectrode", Medical Electronics—February 1991, pages 82-83).

This invention relates also to a method of implanting the above described pacemaker by establishing a direct contact thereof with the heart's epicardium and without having to operate on the epicardium and myocardium of the heart muscle itself and without having to fix by any surgical step, such as sewing, screwing-in, etc., the electrode tip.

A. Carpentier (see: Technique of pacemaker implantation by subxiphoid abdominal approach". Presse Med. 76:75, 1968) and H. O. Trabucco (see: "A new epicardic/myocardic electrode for implantation of pacemakers by modified subxiphoid abdominal approach".

Revista Argentina de Cardiología 42:9, 1974) have already suggested techniques only for surgically implanting catheters having an electrode tip of the hook-shaped type, screw-in type and the like conventional types, using therefor the subxiphoid abdominal approach for the electrode and pluging the connecting end of the electrode into the orthodox pacemaker including a plug receptacle. All such pacemakers being spaced apart from the heart. These surgical techniques allow only the implantation of the catheter into the cardiac muscle, but they were not used for implanting a pacemaker without the use of a catheter. Consequently, in the known techniques the pacemaker had to be located at a spaced apart zone of the heart, such as within the abdominal or thoracic subcutaneous tissues. In other words, it was herethereto necessary to surgically injure the epicardium and myocardium in order to stationary link the electrode tip within the thickness of the heart muscle, so that an acceptable pulse transmission could be achieved.

The method of the present invention takes advantage of the previously disclosed subxiphoid abdominal approach, but has further developed the surgical approach by directly sliding the pacemaker itself into the previously opened pericardial sac, as will be later explained.

As may already be understood, by those skilled in the art, this new surgical technique and method has the following advantages:

1) It is not necessary to surgically injure, as above stated, the cardiac muscle.

2) No second surgical wound is required to form a subcutaneous pacemaker pocket in the human body, to locate the pacemaker into the patient.

3) The proposed surgical procedure is much faster than the pertinent conventional ones.

4) The proposed procedure avoids the potential dangerous risk of a cardiac muscle perforation.

5) No X-ray exposure is required during the surgical approach.

According to the invention, the pacemaker has only to be slipped into the opened pericardial sac to become located below the heart's epicardium outer surface, with its electrode tip in contact with the epicardium outer face in the lower portion of the heart. The pacemaker casing thereby resting on the inner face of the pericardium supported diaphragm. Consequently, the pacemaker becomes immovilized by the actual weight of the heart resting on the diaphragmatic muscle. Once the pacemaker has thus become implanted, the surgical wounds forming the access, are closed and sutured. Only two stitches, to close the pericardial sac, are required. This implanting method does not require to surgically attack and injure the epicardium and myocardium, nor does it need a catheter and the pacemaker is in direct contact with the heart itself.

Thus, a direct transmission of electric pulses, generated by the pacemaker, is achieved from the pacemaker's casing so to say, to the heart.

Within the basic concepts hereinabove outlined, a number of further developments may be conceived, amongst which the following are cited by way of example:

A) The pacemaker's casing may have several shapes and may be provided at its base portion with a reticular structure which facilitates the fibrous tissues which are generated by the patient after the insertion, to penetrate the net-like structure, to thereby more positively anchor the pacemaker's casing in its stimulating position.

B) The periphery of the casing may be provided with a plurality of spaced apart electrode tips connected to the pacemaker's circuitry and which may even be (by a programmer) remote or telemetrically controlled, that is to say that either all the tips or only one or some of them are supplied with electric pulses.

Accordingly, the stimulation may be performed at one selected or at different portions of the heart, either simultaneously or sequentially, in order to select a particular spot or spots of the epicardium, which is or are in best or is or are in optimum position, to transmit the stimulation. It may also be conceived that within the circuitry the different telemetrically controlled electrode tips are connected to different outlets, supplying different ranges of current stimulation. Thus, it will not be necessary to change the position of the casing, in order to obtain, if required, another contact point for transmitting the stimulating pulses, thereby avoiding further complications, such as an "exit block".

C) The casing may be provided with some kind of signal means, such as a thread projecting out of the casing, which facilitates finding the casing after having been implanted for a substantial period (several years) and thereby becoming sustantially surrounded by fibrous tissue generated by the patient's body, in case it should become necessary to withdraw the pacemaker.

D) The casing may be provided with a so called insertion end which facilitates the insertion of the pacemaker between the two aforementioned anatomic structures, namely between the pericardium and the epicardium.

E) The casing may be provided with a small amount of biomedically interesting materials which may be released by remote control, if necessary.

DESCRIPTION OF THE DRAWINGS

FIGS. 14 and 15 are two lateral side views, partially in section, of a portion of a pacemaker according to further embodiment, showing in FIG. 14 a portion of the pacemaker prior to being applied to a heart, while FIG. 15 shows the same portion of the pacemaker applied to the heart.

BRIEF DESCRIPTION OF THE PREFERRED EMBODIMENTS

Figure 1:
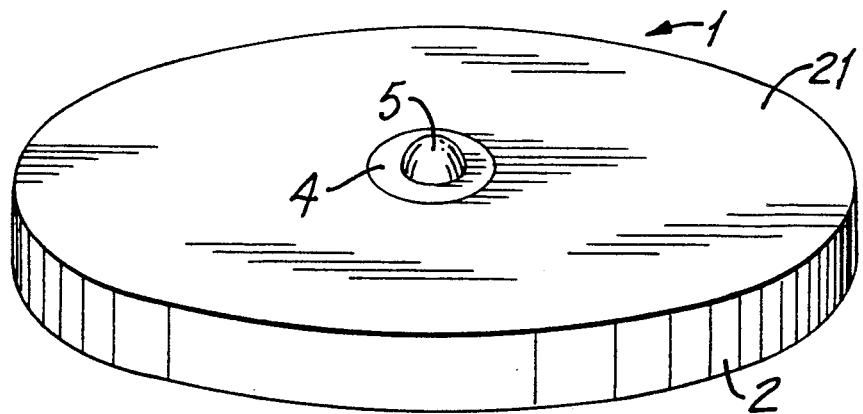
FIG. 1 is a perspective view of a monopolar pacemaker in accordance with the invention, according to a first embodiment.
Figure 2:
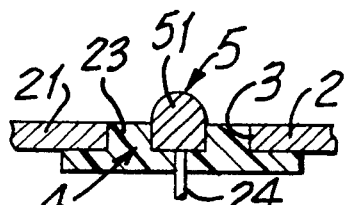
FIG. 2 is a portion, in longitudinal sectional view, of part of the pacemaker's casing, showing the way the electrode tip may be located therein, according to a first lay-out.

Referring first to FIG. 1, it may be seen that the pacemaker 1, according to the first embodiment of the invention, consists of an elliptically shaped casing 2, which is rather thin. The casing 2 is made of a good electricity conducting metal and houses a pulse generator, not shown, since it may be of any of the well known types in the art. Casing 2 (see FIG. 2) has a central perforation 3, wherein a perfectly sealed socket 4 of electricity insulating material is mounted, housing in its central portion an electrode tip 5, the rounded top 5' of which projects out of the socket 4 and of the outer face 2' of casing 2.

From the foregoing it is aparent that the proposed pacemaker 1 has a smaller size, than the equivalent ones known in the art, since it does not need a plug-receptacle.

Figure 17:
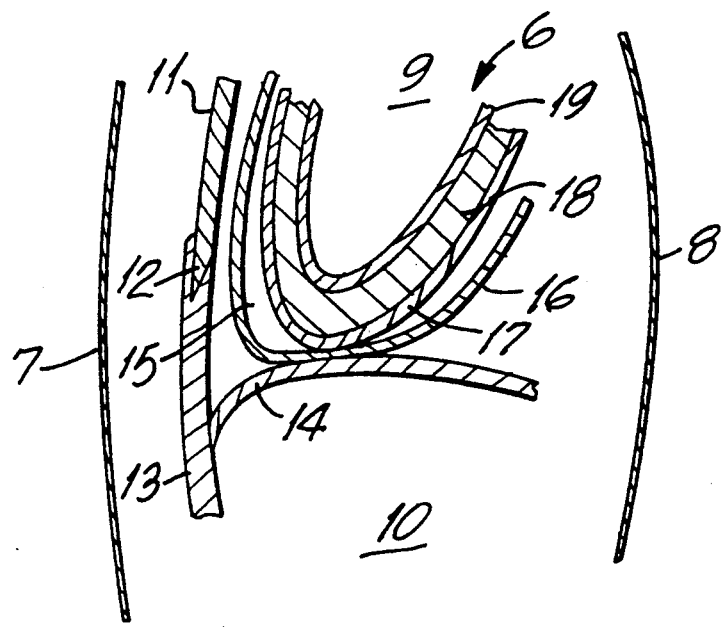
FIGS. 17 and 18 are each a schematical longitudinal sectional view of part of a human body, in the zone corresponding to the heart, which facilitate the explanation of the surgical method of inserting the pacemaker.

In order to better understand the concept of the present invention, reference will now be made to FIGS. 17 and 18 in combination with what has already being described in relationship to FIG. 1. As may be appreciated from FIG. 17, where very schematically the different portions of a human being surrounding the lower portion of the heart 6 are shown and where reference number 7 identifies the front portion of the human body; reference number 8, the rear portion; reference number 9, the upper portion and reference number 10, the lower portion of said human body. The lower portion of the sternon 11 and its cartilagous lower end or xiphoid process 12 which enters the abdominal muscle 13 in turn connected to the diaphragm muscle 14, are likewise shown. The heart 6 is housed in an actual cavity 15 defined by the pericardium 16. The heart 6, is only shown by its lower portion corresponding to a ventricular chamber and its layers of the epicardium 17, myocardium 18 and endocardium 19.

Figure 18:
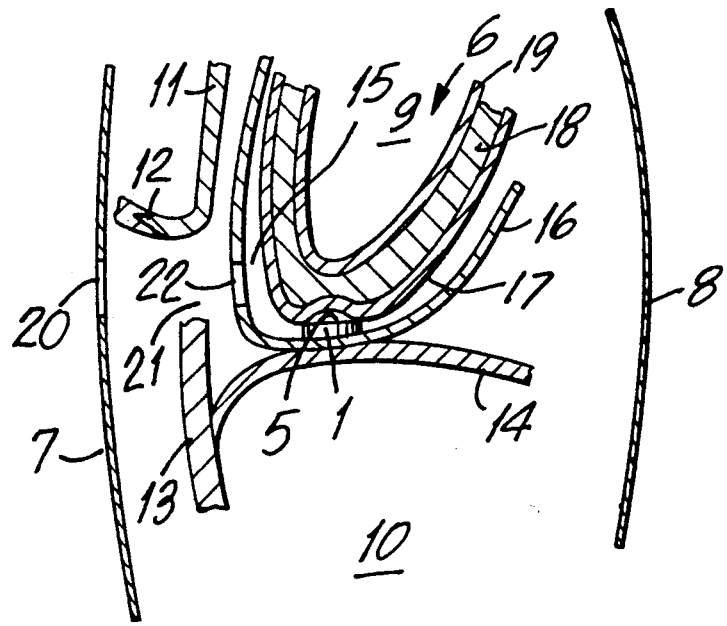

In order to insert and locate the pacemaker 1 of the present invention by using the above referred to surgical subxiphoid approach, that is to say to enter the actual cavity 15, a small opening 20 is formed in the front portion 7 by then opening the abdominal muscle 13, as shown in FIG. 18, to define access opening 21 and turning upwardly the xiphoid process 12 and forming hereafter the access opening 22 in the pericardium 16. Thereafter the pacemaker 1 is inserted via access openings 20, 21 and then just slipped into the actual cavity 15 through opening 22, where it "falls down" so to say by its own weight and moves towards the lower portion of the cavity 15. The surgeon will only have to watch that the electrode tip 5 will face the outer face of the epicardium 17. Once the correct position of the pacemaker 1 has been achieved, the tip 5,5' will, throughout its length be in complementary contact with the epicardium 17. Thereafter the pericardium opening 22 is closed by two stitches and thereafter the surgical wounds 20, 21 are closed in one of the conventional ways. The pacemaker 1 will stay where slipped in, due to its own weight and by the natural clamping pressure exerted by the heart 6 resting on the diaphragm 14 and furthermore due to the already closed pericardial membrane 16 which anatomically surrounds the heart muscle 17, 18, 19. The fibrous tissues which will grow, surrounding the pacemaker 1, as will be readily—understood by those skilled in the art, will further contribute in properly anchoring the pacemaker 1. Pacemakers according to the invention were implanted during 1990 and 1991 in dogs and after 6 months follow up it has been proved that the fibrous tissue did not exert any pressure on the heart of the dogs. No low output heart volume or Pick syndrome were detected.

Thus, it will be readily realized that the pacemaker according to the present invention represents an entirely new principle of stimulating the heart, without requiring any electrode wire (catheter) of the type so far used.

Within the generic concept hereinabove explained, quite a number of additional developments may be conceived and in order to give a guideline in this direction, it is considered advisable to describe some of them, which may be developed in further details as investigations and tests are performed in the future. In other words, a completely new field is herewith opened as to the way of stimulating the heart and who knows in the future as the miniaturization technique progresses, such pacemakers may even be applied to other organs within the human body, which require pertinent electric stimulation. Therefore the expression "pacemaker" has to be interpreted in such a broad way.

Returning now to FIG. 2, it may be added that the socket 4 has a central cylindrical projection 23, having a height equal to the thickness of the casing 2, where the perforation 3 exists, in order to thus achieve a perfect sealing between the casing 2 and the socket 4 and forming thereby a smooth outer surface of the casing. The electrode tip 5 emerges with a rounded top portion 5' from the outer face 2' and is connected by its inner end portion to a wirea 24 which in turn is connected to the pulse generating circuitry (not shown) housed in casing 2.

Figure 3:
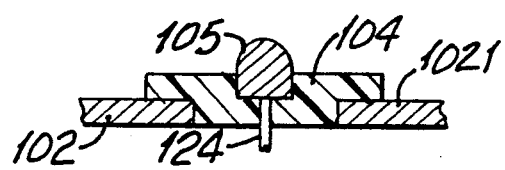
FIG. 3 is a longitudinal sectional view, similar to FIG. 2, but showing the mounting of the electrode tip according to a second lay-out and including biomedically interesting materials, releaseable by remote control.

Obviously, several ways of mounting the electrode tip within the casing may be conceived; merely by way of example in FIG. 3 an embodiment is shown where the socket 104 covers the upper portion or surface 102' of casing 102, thus providing an enlarged sealing surface between the socket 104 and the casing 102. This particular type of socket defines a larger peripheral outer portion which is not acting purely as a seal, but it could also be made of a poly(N-methylpyrrole)/poly(styrenesulfonate) conducting polymer system which can store small quantities of biomedically interesting materials which can be released by means of an electrical potential change as disclosed in the aformentioned Medical Electronics magazine. The basic concept is to bind molecules (i.e., neuro-transmitters) into a polymer membrane and release the biomolecules as needed by changing an electrical potential applied across the polymer. In other words, the drug counter-ions can then be released in vivo by controlled electrical potential changes which are suppliable by the circuitry of the pacemaker and upon exciting the pertinent portion through remote or telemetric control.

Figure 5:
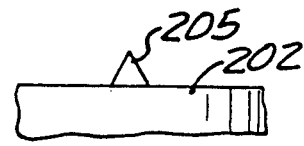
FIGS. 5, 6 and 7 are respective side elevations of several electrode tips, forming part of the pertinent portion of the pacemaker's housing.

The shape of the electrode tips may be changed in order to achieve suitable cardiac stimulations. Thus, in FIG. 5 an electrode tip is shown having a conical point and which projects out of casing 202.

Figure 6:
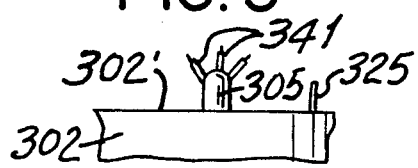

In FIG. 6 part of a casing 302 is shown, the upper face 302' of which is provided with one (or several) anchoring pin(s) 325 to penetrate into the epicardium. The electrode tip 305 is also provided with pin-like projections 341 which may be electricity conducting or nonconducting. These pins will increase the capacity of electricity transmision or simply acting as additional anchoring devices.

Figure 7:

In FIG. 7 another type of tip is shown, more particularly having a concave end portion, whereby a different distribution of the electric current is achieved.

Figure 8:
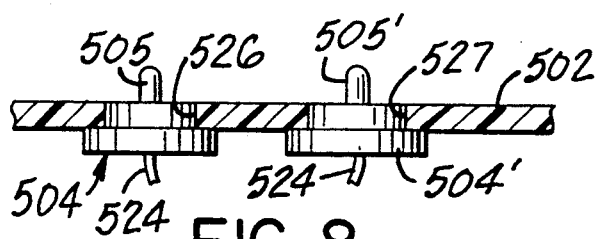
FIG. 8 is a longitudinal section of a portion of a pacemaker's housing with a bipolar arrangement of electrode tips.

In all the embodiments so far described, one has started from the concept that the pacemaker is of a monopolar type, that is to say an electricity conducting casing 2 is suggested as having a single suitable electrode tip 5 insulated from casing 2, so that, upon said tip 5 emitting a negative current the circuit is closed through the patient's body to the casing which represents the anodic pole. However, it is obviously possible to provide a pacemaker in accordance with the present invention, being of the bipolar type, using an anodic electrode and another cathodic electrode. Bipolar pacemakers are well known in the art and therefor no further information is herewith required. It will be sufficient to refer to FIG. 8, where casing 502 is made of electricity insulating material and having two spaced apart openings 526 and 527 in which pertinent sockets 504, 504' are housed, with the electrode tips 505, 505', respectively connected to the pulse generator (not shown) through wires 524, 524'. Wire 524 corresponds for instance to the cathodic pole and wire 524' to the anodic pole of the circuit.

Figure 9:
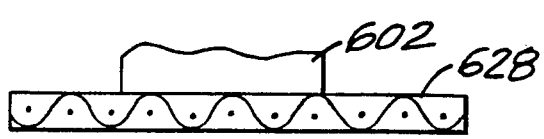
FIG. 9 is a partial longitudinal section of a portion of a pacemaker's housing, according to a third embodiment.

In connection with the anchoring of the casing within the actual cavity 15 and the forming of the fibrous tissue as previously explained in relationship to FIG. 18, it has also been thought that it would be possible to facilitate the anchoring of the casing 602 (FIG. 9) for instance by providing below the base portion of the casing a net-like structure 628, for instance made of inert plastic and which projects beyond the periphery of casing 602. Thus, the fibrous tissues which are generated by the patient, grow into the holes of the net-like structure 628 in the portion surrounding casing 602, improving thus the anchorage of the pacemaker.

Figure 10:
FIG. 10 is a side elevation of a portion of a pacemaker, according to a fourth embodiment.

In FIG. 10 a portion of casing 702 is shown provided with an X-ray opaque thread 729 acting as signal means. The idea is that the fibrous tissue which will be surrounding the casing 702 may hide the pacemaker. In case it should become necessary, at a later stage, to withdraw the pacemaker, for instance because its battery is depleted, which nowadays usually happens after 8 to 10 years of use, the surgeon may easily and quickly find the end of thread 729, usually projecting out of the fibrous tissue and thereby, following its path, tracing the pacemakers' casing, within the shortest possible time.

Figure 11:
FIG. 11 is a side elevation of a portion of a pacemaker, according to a fifth embodiment.

In FIG. 11 a casing 802 is shown, having a pointed front end portion 830 to facilitate the insertion through access opening 22, especially in those cases where the actual cavity 15 is of small size, due to adherences.

Figure 12:
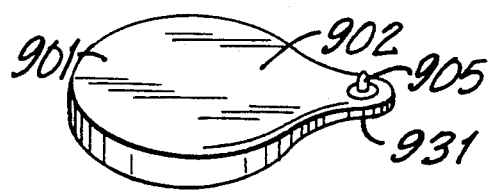
FIG. 12 is a perspective view of a pacemaker, according to a sixth embodiment.

FIG. 12 shows a pacemaker 901 including a casing 902 having a projection or nose portion 931 of small thickness, which houses the electrode tip 905. This nose portion 931 is bendable, so that the surgeon, during the insertion of the pacemaker 901, may exert a pressure on the nose portion 931 in order to bend it towards the epicardium and thereby achieving a better electric contact of the electrode tip 905 with the epicardium.

Figure 13:
FIG. 13 is a side elevation of a pacemaker, according to a seventh embodiment.

FIG. 13 shows a casing 1000 being of biconcave shape and having its electrode tip 1005 at its peripheral portion. Thus, a casing is provided which has an anatomical curve, shaped to be complementary to the facing organs of the patient.

Figure 14:
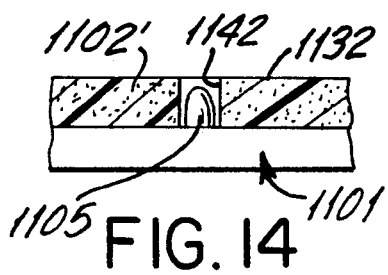
Figure 15:
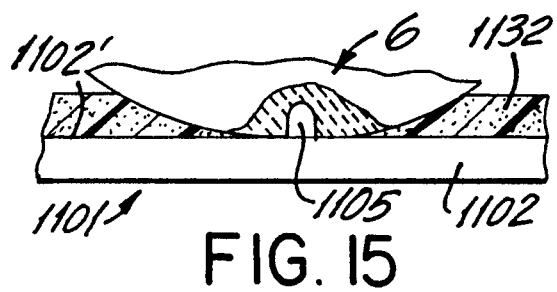

FIGS. 14 and 15 disclose another idea, where it is desired to protect the tip 1105, so that during the insertion of the pacemaker it does not project out of the upper face which has to be slid along the epicardium towards its final position. To this end, the upper face 1102' of casing 1102 is sheathed with a sponge-like material 1132, which upon being uncompressed, that is to say without being subject to any pressure, has a height slightly larger than the projecting electrode tip 1105 and which tip becomes thus totally housed within opening 1142 of said sponge-like material 1132, as shown in FIG. 14. Upon the heart 6 becoming located on top of the pacemaker 1101, as shown in FIG. 15, the pertinent sponge-like material 1132 is compressed, whereby the electrode tip 1105 contacts the epicardium and the compressed sponge-like material 1132 acts as an additional frictional inmovilizer of the pacemaker 1101 in relationship to the pertinent heart portion.

Figure 4:
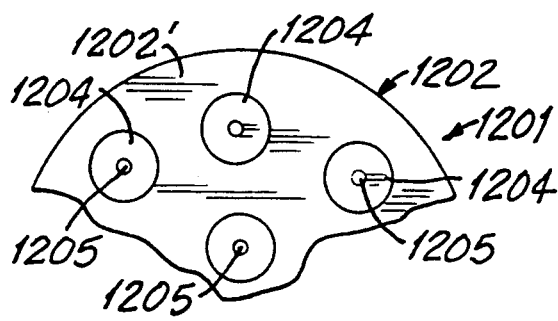
FIG. 4 is a top plan view of a portion of a pacemaker, according to a second embodiment.

In FIG. 4, the upper face 1202' of the casing 1202 of a pacemaker 1201 is shown. A plurality of electrode tips 1205, flush with the upper or outer face of its pertinent socket 1204 and upper face 1202' are shown. These tips 1205 are spaced apart amongst themselves. All these electrode tips are capable of establishing contact with the epicardium and all these electrode tips are of the same polarity. Thus, it is possible to stimulate at will, different points of the heart to determine which tip will provide the optimum electric pulse transmission. Presumably only one electrode will finally become active.

Figure 16:
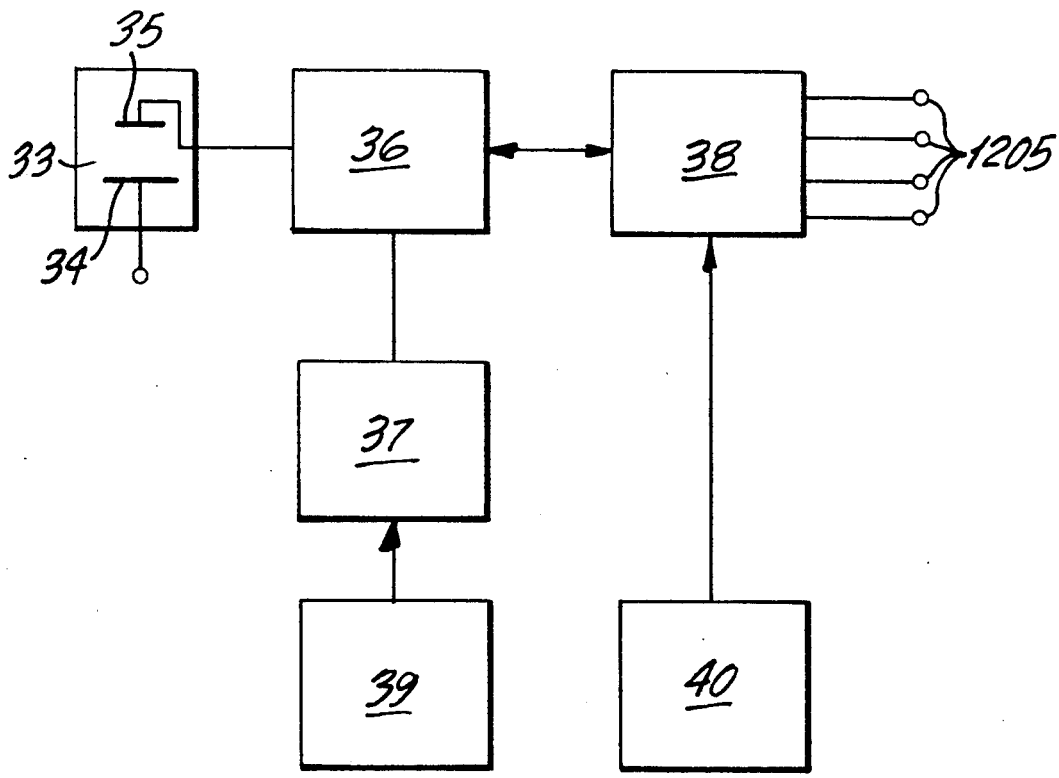
FIG. 16 is a block diagram, showing an electronic circuit applicable to the second embodiment shown in FIG. 4.

It is also conceivable to supply to several of those tips, pulses of different values. To this end a commanding circuit may be provided within a pulse generator which can carry out these steps. In fact, and with reference to FIG. 16, an electronic, block, remote controlled, circuit is shown, where block 33 represents a supply source such as a battery having its positive pole connected to the casing of the pacemaker, if such casing is made of electricity conducting material or if not, it could be connected to another of the electrode tips if the pacemaker is of the bipolar type, as shown for instance in FIG. 8. The negative pole 35 is connected to a pulse generator represented by block 36 which is connected on the one hand to a control circuit 37 and on the other hand to a switching and measuring circuit 38. Both, the control circuit 37 as well as the switching and measuring circuit 38 are controlled by respective telemetric remote controlling devices 39, 40. The switching and measuring circuit 38 is connected through several outlets to the electrode tips 1205. It thus becomes aparent to those skilled in the art, that the surgeon may vary at will the features of the pulses to be emitted by means of the remote controls 39, 40 be it to determine which of the electrode tips 1205 shall be definitely active, be it to stimulate series of pulses of different values through several tips 1205 forming part of the casing 1202 of the pacemaker 1201 or any other suitable combination of different types of pulses, different output values, be they monopolar or bipolar, using simultaneously one or several electrode tips.

We claim:

1. A pacemaker usable to stimulate an organ such as the heart comprising a suture-free casing housing a pulse generator connected to at least one electrode tip forming part of the outer surface of said casing and being electrically insulated therefrom, said electrode tip comprising means for directly entering into non-perforating contact with the epicardium of the heart without piercing the epicardium.

2. The pacemaker of claim 1, said casing having an upper outer surface including at least one opening wherein an electricity insulating socket is sealingly housed, said electrode tip projecting out of said upper outer surface through said socket.

3. The pacemaker of claim 2 wherein said socket is provided with means for remote controllable release of biomedical materials.

4. The pacemaker of claim 1, wherein the upper outer surface includes a plurality of spaced apart openings, each housing a socket and an electrode tip.

5. The pacemaker of claim 4, wherein each electrode tip is independently excitable.

6. The pacemaker of claim 4, wherein said electrode tips are successively excitable with different outputs.

7. The pacemaker as claimed in claim 1, wherein the casing thereof is provided with anchoring means.

8. The pacemaker of claim 1, wherein said casing is provided with signal means enabling to trace said pacemaker upon being surrounded by fibrous tissues.

9. The pacemaker of claim 1, wherein said casing has a pointed front end portion to facilitate the slipping-in of said pacemaker into the pericardial sac of the heart.

10. The pacemaker of claim 1, wherein said casing includes a projecting, bendable nose portion, housing said electrode tip.

11. The pacemaker of claim 1, wherein said casing is biconcavely shaped.

12. The pacemaker of claim 1, wherein said casing has a net-like anchoring structure.

13. The pacemaker of claim 1, wherein said electrode tip is surrounded by a compressible sponge-like material.

14. A method of direct contact implanting of a pacemaker onto the epicardium outer surface of a heart of a human patient, said pacemaker comprising a casing housing a pulse generator connected to at least one electrode tip forming part of the outer surface of said casing and being electrically insulated therefrom, said electrode tip comprising means for directly entering into non-perforating contact with the epicardium of the heart, said method comprising the steps of providing access to the patient's pericardium by a subxiphoid abdominal approach which comprises opening said pericardium to gain access to the pericardial sac, slipping said pacemaker into the cavity existing between the inner surface of said pericardium and the outer surface of said epicardium so that said pacemaker is located at the lower portion of the pericardial sac and is in contact with said heart, establishing a good electric contact with the epicardium and thereafter closing the opening in said pericardium.

* * * * *